United States Patent
Morimoto et al.

(10) Patent No.: US 8,114,672 B2
(45) Date of Patent: Feb. 14, 2012

(54) METHOD FOR ANALYZING ANTIMONY CONTAINED IN GLASS

(75) Inventors: Sayaka Morimoto, Yokohama (JP); Miyuki Takenaka, Yokohama (JP); Mitsuhiro Oki, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/888,657

(22) Filed: Sep. 23, 2010

(65) Prior Publication Data
US 2011/0217782 A1    Sep. 8, 2011

(30) Foreign Application Priority Data
Mar. 8, 2010   (JP) ................................ 2010-051110

(51) Int. Cl.
*G01N 33/20*   (2006.01)
(52) U.S. Cl. .......................................... 436/73; 75/703
(58) Field of Classification Search .................... 436/73; 75/703
See application file for complete search history.

(56) References Cited

U.S. PATENT DOCUMENTS
2011/0017020 A1*   1/2011   Homma et al. .................. 75/403

FOREIGN PATENT DOCUMENTS
JP    2000-317205    11/2000
* cited by examiner

*Primary Examiner* — Robert J Hill, Jr.
*Assistant Examiner* — Dwan A Gerido
(74) *Attorney, Agent, or Firm* — Turocy & Watson, LLP

(57) ABSTRACT

According to one embodiment, there is provided a method of analyzing antimony contained in glass according to its valency. This method includes milling glass containing antimony into a glass powder, weighing the glass powder and dissolving the glass powder by using hydrofluoric acid and hydrochloric acid to obtain a glass solution, masking hydrofluoric acid by adding aluminum ions to the glass solution, adding sodium borohydride and hydrochloric acid to the glass solution in which hydrofluoric acid is masked to generate a hydride of antimony (III), determining a concentration of antimony (III) contained in the glass solution based on the hydride, determining a total concentration of antimony contained in the glass solution and calculating a difference between the concentration of antimony (III) and the total concentration of antimony to obtain a concentration of antimony (V) from the difference.

4 Claims, 2 Drawing Sheets

METHOD FOR ANALYZING ANTIMONY CONTAINED IN GLASS

CROSS-REFERENCE TO RELATED APPLICATIONS

This application is based upon and claims the benefit of priority from Japanese Patent Application No. 2010-051110, filed Mar. 8, 2010; the entire contents of which are incorporated herein by reference.

FIELD

Embodiments described herein relate generally to a method for analyzing antimony contained in glass according to its valency.

BACKGROUND

Regulations with regards to chemical substances have been more rigorous along with growing worldwide environmental problems. For example, the use of six special harmful substances is prohibited by EU:RoHS (European Restriction of Hazardous Substances in Electrical and Electronic Equipment). Further, chemical substances including Substances of Very High Concern (SVHC) are controlled by REACH (Registration, Evaluation, Authorisation and Restrictions of Chemicals) which is a regulation regarding the registration, evaluation, authorisation and restrictions of chemical substances. As mentioned above, in recent years, regulations with regards to chemical substances have been more rigorous.

In the meantime, antimony is added as a clarifying agent to glass which we use frequently. Antimony is an element which is a homologue of arsenic and can be probably a substance of SVHC regulated by REACH. Because antimony is different in toxicity depending on valency, it is desired to develop a method enabling the analysis of antimony according to its valency.

For analyzing antimony (III) and antimony (V) according to its valency, an analytical method which is a combination of the solvent extraction and hydride separation ICP method has been tried so far (for example, JP-A 2000-317205 (Kokai)).

However, the above method has the drawback that in the case of intending to analyze antimony contained in glass according to its valency, it is necessary to dissolve the glass once by using a hydrofluoric acid solution and then to measure antimony contained in the hydrofluoric acid solution, and this operation cannot be carried out in the above method.

DETAILED DESCRIPTION

According to one embodiment, there is provided a method of analyzing antimony contained in glass according to its valency. This method includes milling glass containing antimony into a glass powder, weighing the glass powder and dissolving the glass powder by using hydrofluoric acid and hydrochloric acid to obtain a glass solution, masking hydrofluoric acid by adding aluminum ions to the glass solution, adding sodium borohydride and hydrochloric acid to the glass solution in which hydrofluoric acid is masked to generate a hydride of antimony (III), determining a concentration of antimony (III) contained in the glass solution based on the hydride, determining a total concentration of antimony contained in the glass solution and calculating a difference between the concentration of antimony (III) and the total concentration of antimony to obtain a concentration of antimony (V) from the calculated difference.

Embodiments of the present invention are explained below in reference to the drawings.

Figure 1:
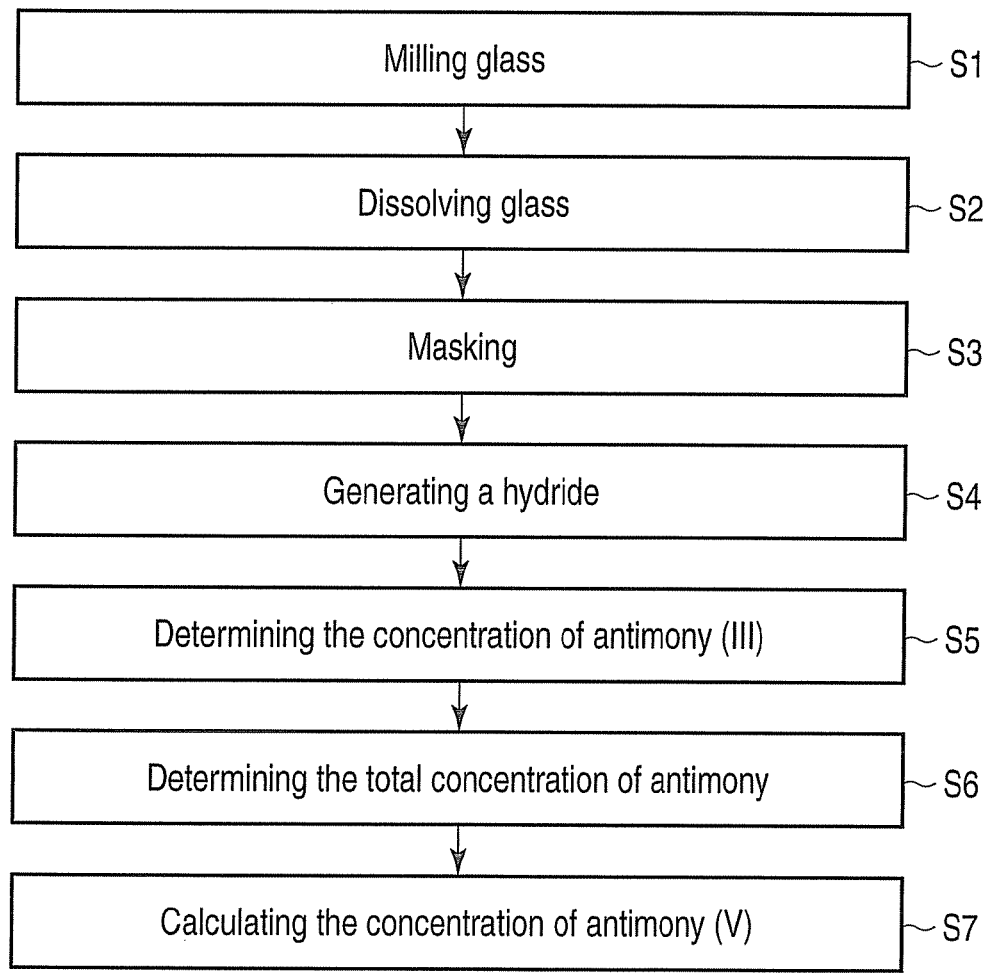
FIG. 1 is a flow chart showing an example of a method of analyzing antimony contained in glass according to its valency.

A method according an embodiment comprises the steps S1 to S7 as shown in FIG. 1. The steps S1 to S3 are carried out for the purpose of preparing samples and the steps S4 to S7 are carried out for the purpose of analyzing the concentrations of these samples.

(S1: Step of Milling Glass)

Glass is milled in a mortar into a fine glass powder such that it is dissolved in S2 which will be shown below. As the glass to be subjected to a test, glass usually used for instruments or equipment is used. In this case, the glass powder is screened to obtain a glass powder having a particle diameter of 106 μm or less.

(S2: Step of Dissolving Glass)

The glass powder obtained in S1 is weighed to prepare a glass solution by using hydrofluoric acid and hydrochloric acid. The glass powder is placed in a container such as Teflon (registered trademark) beaker and hydrofluoric acid and hydrochloric acid is added to the container, and the container is heated to dissolve the glass powder.

The glass powder may be weighed by using the weighing method generally used in precision analysis such as a method using an electronic balance. Further, the concentration of hydrofluoric acid to be used is preferably 2.5 to 3.0 M so as not to hinder the generation of a hydride in the step of generating a hydride which will be explained later. Furthermore, the concentration of hydrochloric acid is preferably 8 to 10 M. The container is preferably heated at 100 to 200° C.

(S3: Step of Masking Hydrofluoric Acid)

Fluoride ions in the glass solution obtained in S2 are masked by aluminum ions. The masking here means treatment carried out to form a complex of the fluoride ion and aluminum ion. By masking the fluoride ion by aluminum, a hydride of antimony can be generated without any influence of fluoride ions in the step S4 which will be explained later.

Specifically, a water soluble one such as an aluminum chloride solution is added to the glass solution. After the masking, pure water is added to obtain a predetermined amount of the solution.

(S4: Step of Generating a Hydride)

This is a step of hydrogenating antimony (III) contained in the solution obtained in the step S3 to generate a hydride (stibine). Antimony (III) in the solution is measured by the so-called hydride generation method.

Figure 2:
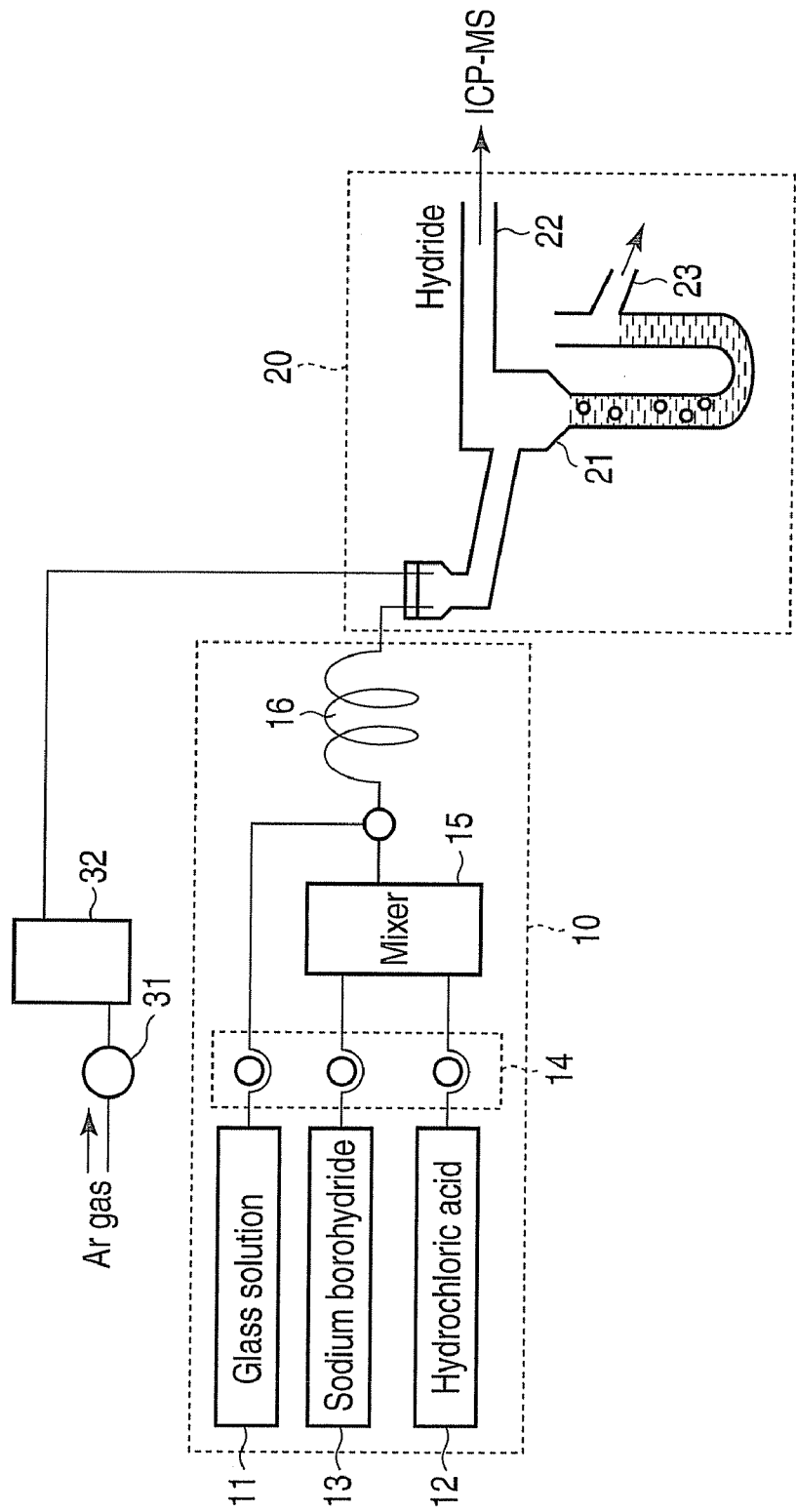
FIG. 2 is a conceptual view of a hydride generation apparatus and an ICP-mass spectrometer.

FIG. 2 shows an example of the hydride generation apparatus. A hydride generation apparatus 1 comprises a sample/reagent mixing reaction part 10 and a gas-liquid separating part 20. In the sample/reagent mixing reaction part 10, a glass solution 11 which is a subject of measurement is reacted with a sodium borohydride 12 and a hydrochloric acid 13 as reagents used to generate hydride gas. The reaction is run by introducing the glass solution 11 into a reaction tube 16 through a peristaltic pump 14, introducing the sodium borohydride 12 and hydrochloric acid 13 into a mixer 15 through the peristaltic pump 14 to mix the both in advance and the mixed reagents are introduced into the reaction tube 16.

The reaction product obtained by the reaction in the reaction tube 16 is introduced into a gas-liquid separating tube 21 of the gas-liquid separating part 20. Further, argon which is carrier gas is introduced into the gas-liquid separating tube 21 through a pressure gauge 31 and a flow meter 32. The hydride contained in the reaction product is discharged from a discharge port 23 of the gas-liquid separating tube 21 and flowed into an ICP-mass spectrometer. Excess liquid is drained from a discharge port 23 of the gas-liquid separating tube 21.

In this embodiment, antimony (III) in the solution is made into a hydride (stibine) by hydrogen generated by the reaction between sodium borohydride and hydrochloric acid with the following reaction formulae.

$$NaBH_4 + HCl + 3H_2O \rightarrow H_3BO_3 + NaCl + 8H$$

$$Sb(III) + 8H \rightarrow SbH_3 + 5/2 H_2$$

Because stibine is gasified at normal temperature, it can be separated by the gas-liquid separating tube. With regard to stibine generating condition, in this case, it is preferable to blend 1 mol/L hydrochloric acid with a mixture solution comprising 1% sodium borohydride and 0.5% sodium hydroxide.

(S5: Step of Determining the Concentration of Antimony (III))

This is a step of determining the concentration of antimony (III) based on the hydride (stibine) obtained in Step S4. As the method of measuring a hydride quantitatively, known instruments such as an ICP-optical emission spectrometer, ICP-mass spectrometer and atomic absorption spectrometer are used. However, because antimony contained in glass is in trace amount, it is preferable to use an ICP-mass spectrometer. In the case of using any of these instruments, a sample which is the subject of analysis is measured quantitatively after making a calibration curve obtained by correlating the concentration of antimony with the intensity of signals, to calculate the concentration of antimony (III).

(S6: Step of Determining the Total Concentration of Antimony)

This is a step of determining the total concentration of antimony contained in the glass solution obtained in S3. As the method of determining the concentration, known instruments such as an ICP-optical emission spectrometer, ICP-mass spectrometer and atomic absorption spectrometer are used in the same manner as in the case of S5 to calculate the concentration from the intensity by using the calibration curve method.

(S7: Step of Calculating the Concentration of Antimony (V))

A difference between the total concentration of antimony obtained in S6 and the concentration of antimony (III) obtained in S5 is calculated to thereby obtain the concentration of antimony (V).

The above steps S1 to S7 make it possible to analyze antimony contained in glass according to its valency.

EXAMPLES

Preparation of a Glass Solution

Antimony trichloride was dissolved in 3M hydrochloric acid to prepare a standard antimony (III) solution. Potassium hexahydroxoantimonate (V) was dissolved in pure water to prepare a standard antimony (V) solution.

Quartz glass was milled in a mortar into a powder and this glass powder was sieved to obtain glass powder having a particle diameter of 106 μm or less. 50 mg of the sieved glass powder was weighed. Antimony (III) and antimony (V) were each added in an amount of 10 μg/L to the weighed glass powder, and hydrofluoric acid and hydrochloric acid were further added to the glass powder, followed by heating to dissolve them, thereby obtaining a glass solution.

Example 1

3 mL of a 1 wt % aluminum chloride solution was added to the above glass solution, which was then diluted with pure water to be a volume of 50 mL, thereby obtaining a masking treated solution.

In a hydride generating apparatus (trade name: THG-1200, manufactured by SII Nanotechnology Inc.), 1 mol/L of hydrochloric acid was mixed in a mixed solution of 1% sodium borohydride and 0.5% sodium hydroxide through a peristaltic pump, and this solution was reacted with the above masking treated solution. Generated stibine was measured quantitatively by an ICP-mass spectrometer (trade name: SPQ9000, manufactured by SII Nanotechnology Inc.).

The concentration of antimony (III) was calculated from the intensity by using the calibration curve method. As a result, the amount of antimony (III) was 8.4 μg/L. The amount of antimony (III) to be added was 10 μg/L, therefore the yield was 84.0%. The yield here is the ratio of the resulting concentration of antimony (III) to the concentration of antimony (III) to be added to the glass solution.

Comparative Example 1

Without performing the masking treatment in the operation of Example 1, the concentration of antimony (III) was determined by using the hydride generation apparatus and ICP-mass spectrometer. The concentration of antimony (III) was 0.24 μg/L. The yield was calculated to be 2.4%.

Comparative Example 2

In the operation of Example 1, boric acid was used in place of aluminum chloride as the masking agent. This resulted in a rise in background, so that exact measurement could not be attained.

As mentioned above, the yield of antimony (III) could be increased by masking hydrofluoric acid by aluminum chloride. This has made it possible to analyze antimony contained in glass according to its valency with high accuracy by the hydride generating method.

According to the above embodiments or examples, a method of performing the analysis of antimony according to its valency and quantitative analysis of antimony in glass with high accuracy can be provided.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of analyzing antimony contained in glass, comprising:
   milling glass containing antimony into a glass powder;
   weighing the glass powder and dissolving the glass powder by using hydrofluoric acid and hydrochloric acid to obtain a glass solution;

masking hydrofluoric acid by adding aluminum ions to the glass solution;

adding sodium borohydride and hydrochloric acid to the glass solution in which hydrofluoric acid is masked to generate a hydride of antimony (III);

determining a concentration of antimony (III) contained in the glass solution based on the hydride;

determining a total concentration of antimony contained in the glass solution; and calculating a difference between the concentration of antimony (III) and the total concentration of antimony to obtain a concentration of antimony (V) from the difference.

2. The method according to claim 1, wherein masking the hydrofluoric acid is carried out by adding an aluminum chloride solution.

3. The method according to claim 1, wherein determining the concentration of antimony (III) is carried out by using an inductively coupled plasma-mass spectrometer.

4. The method according to claim 1, wherein determining of the total concentration of antimony is carried out by using an inductively coupled plasma-mass spectrometer.

* * * * *